United States Patent [19]
Golden

[11] Patent Number: 5,226,530
[45] Date of Patent: Jul. 13, 1993

[54] PRELUBRICATED URINARY CATHETER AND PACKAGE ASSEMBLY

[76] Inventor: John H. Golden, 2939 Chesterfield Way, Conyers, Ga. 30208

[21] Appl. No.: 855,900

[22] Filed: Mar. 23, 1992

[51] Int. Cl.⁵ .............................................. B65D 85/08
[52] U.S. Cl. ...................................... 206/210; 53/428; 206/364
[58] Field of Search ............... 206/205, 210, 363, 364, 206/438, 803; 53/428

[56] References Cited

U.S. PATENT DOCUMENTS

| | | | |
|---|---|---|---|
| 3,648,704 | 3/1972 | Jackson | 206/364 |
| 3,750,875 | 8/1973 | Juster | 206/364 |
| 3,794,042 | 2/1974 | De Klotz et al. | 206/210 |
| 3,854,483 | 12/1974 | Powers | 206/210 |
| 3,934,721 | 1/1976 | Juster et al. | 206/364 |
| 3,967,728 | 7/1976 | Gordon et al. | 206/210 |
| 3,978,983 | 9/1976 | Brezette | 206/210 |
| 4,772,275 | 9/1988 | Erlich | 206/364 |
| 4,811,847 | 3/1989 | Reif et al. | 206/210 |
| 4,923,061 | 5/1990 | Trombley, III | 206/364 |
| 5,131,537 | 7/1992 | Gonzales | 206/364 |

Primary Examiner—Jimmy G. Foster
Attorney, Agent, or Firm—B. J. Powell

[57] ABSTRACT

A prelubricated urinary catheter and package assembly for use in draining the bladder through the urethra comprising an elongate catheter tube with a lubricant on the projecting end thereof and a package assembly receiving the catheter therein an arrangement for isolating the lubricant on the projecting end of the catheter from the rest of the catheter in the catheter receiving cavity.

5 Claims, 2 Drawing Sheets

PRELUBRICATED URINARY CATHETER AND PACKAGE ASSEMBLY

BACKGROUND OF THE INVENTION

This invention relates generally to catheters and more particularly to prelubricated intermittent catheters.

Heretofore, single use catheters designed for intermittent or self catheterization have been supplied without an insertion lubricant thereon. This is because the lubricant is designed to liquify at body temperature and frequently becomes sufficiently liquid during storge to coat the inside of the package carrying the catheter and also the complete catheter. As a result, the prior art supplied the lubricant in a separate container. This required the lubricant to be applied by the user after the catheter was removed from the sterile package in which the catheter is supplied. Not only was this inconvenient for the user but also allowed the lubricant in the tube to become contaminated thereby spreading the contamination to subsequently used catheters when the lubricant was applied.

SUMMARY OF THE INVENTION

These and other problems and disadvantages associated with the prior art are overcome by the invention disclosed herein by providing a urinary catheter and package assembly which provides a prelubricated catheter for intermittent use to facilitate the use thereof. The lubricant preapplied to the projecting end of the catheter is isolated from the rest of the catheter and package so that the lubricant coats only the desired portion of the catheter and does not migrate to undesirable portions of the package. In those instances where it is desirable to precoat the entire catheter with lubricant, the catheter is sealed in a single cavity in the package.

The apparatus of the invention is directed to a prelubricated urinary catheter and package assembly for use in draining the bladder through the urethra comprising an elongate catheter tube with a lubricant on the projecting end thereof and a package assembly defining a catheter receiving cavity therein with isolation means for isolating the lubricant on the projecting end of the catheter from the rest of the catheter in the catheter receiving cavity. The package assembly may include a primary receptacle defining a primary catheter receiving cavity therein for stowing the catheter with the isolation means comprising a secondary receptacle defining a secondary projecting end receiving cavity therein receiving the projecting end of the catheter with the lubricant thereon to isolate the lubricant from the primary cavity. Alternatively, the package assembly may include a single catheter receiving cavity receiving the catheter with the isolation means dividing the catheter receiving cavity into first and second portions so that the projecting end of the catheter with the lubricant thereon is housed in the second portion of the cavity and the rest of the catheter is housed in the first portion of the cavity.

These and other features and advantages of the invention will become more clearly understood upon consideration of the following detailed description and accompanying drawings wherein like characters of reference designate corresponding parts throughout the several views and in which:

These figures and the following detailed description disclose specific embodiments of the invention, however, it is to be understood that the inventive concept is not limited thereto since it may be embodied in other forms.

DETAILED DESCRIPTION OF ILLUSTRATIVE EMBODIMENTS

Figure 1:
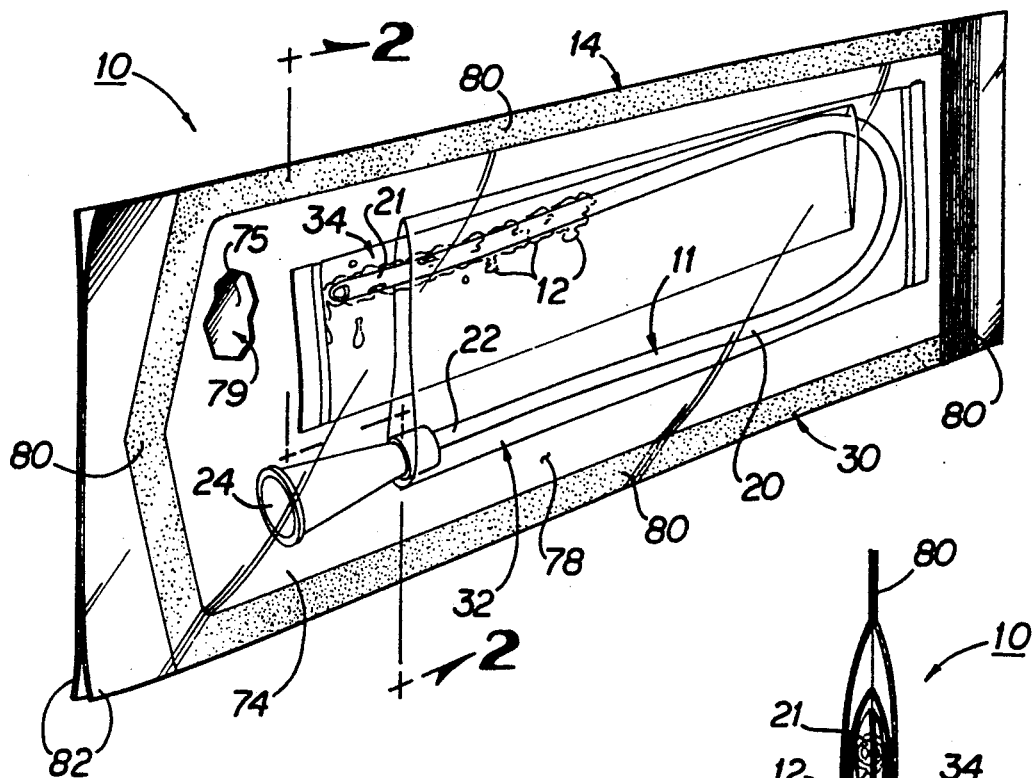
FIG. 1 is a perspective view of a first embodiment of the invention.

Referring to FIG. 1, it will be seen that the catheter and package assembly 10 includes a catheter 11 with a lubricant 12 thereon and a package assembly 14 that carries the catheter therein. The lubricant 12 is preapplied to the catheter 11 so that the user simply has only to remove the catheter 11 from the package assembly 14 for use.

The catheter 11 corresponds to those catheters currently in use for intermittent catheterization. Catheter 11 includes an elongate catheter tube 20 with a projecting end 21 and an opposed drainage end 22. The drainage passage extends through the tube 20 from the projecting end to the drainage end so that once the projecting end 21 enters the bladder, the bladder can drain through the catheter. The drainage end 22 of the catheter tube 20 may be left plain or equipped with a receptacle connector 24 as shown in the figures.

The lubricant 12 is that typically used with catheters and is designed to liquify at body temperature. The lubricant 12 is applied to the catheter tube 20 at the projecting end 21 thereof and a prescribed distance along the catheter tube from the projecting end. The package assembly 14 is designed to prevent the lubricant 12 from completely coating the catheter or completely coating the inside of the package assembly 14 and at the same time to provide a sealed sterile enclosure for the lubricated catheter. Preventing transfer of the lubricant 12 to other portions of the catheter is desirable since the presence of lubricant on portions of the catheter other than the projecting end 21 would cause those surfaces to become slippery and increase the manual dexterity level necessary for proper insertion of the catheter during use.

The first embodiment of the package assembly 14 shown in FIGS. 1-4 includes an outside enclosing receptacle 30, an intermediate primary receptacle 32 and an inside secondary receptacle 34. The secondary receptacle 34 serves as the isolating means to prevent the lubricant 12 flowing away from the projecting end 21 of the catheter 11, the primary receptacle 32 serves to contain the catheter 11 with the secondary receptacle 34 thereon while maintaining the catheter formed in the U-shaped configuration for stowing, yet allowing access thereto, and the enclosing receptacle 30 serves to contain the catheter 11 in the primary and secondary receptacles 32 and 34 to provide a sterile environment for the catheter until it is used.

Figure 4:
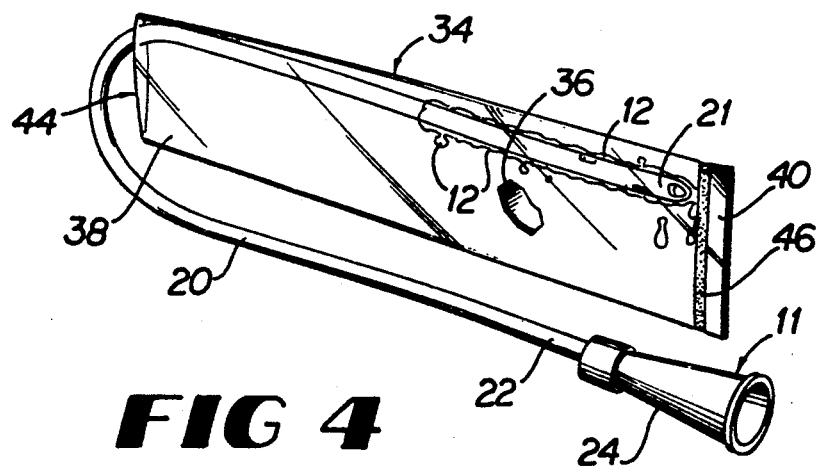
FIG. 4 is a perspective view similar to FIG. 2 with the intermediate primary receptacle removed.

The secondary receptacle 34 comprises a secondary tubular sheath 38 with one end 40 closed to define a secondary projecting end receiving cavity 36 therein and with the other end open to define a secondary access opening 44 through which the lubricated projecting end 21 is inserted as seen in FIG. 4. The elongate secondary receptacle 34 serves as a means for isolating the lubricant 12 and lubricated projecting end 21 of the catheter 11 from the rest of the catheter disposed outside of the secondary receptacle 34. The secondary receptacle 34 may be formed from a flexible, heat sealable plastic tubular film with the closed end sealed by secondary heat weld 46. Any convenient alternative construction may be used as long as it defines a cavity into which the projecting end of the catheter will fit, for example, an elongate rigid hollow tube with an open end and a closed end. Prior to insertion of the catheter into the bladder, the lubricated projecting end 21 is removed from the secondary receptacle 34 by sliding it out of the secondary receptacle receiving cavity 36 through the secondary access opening 44. The projecting end thus emerges from the secondary receptacle 34 coated with the lubricant 12 ready for use and leaving a residue of the lubricant within the secondary receptacle 34.

Figure 3:
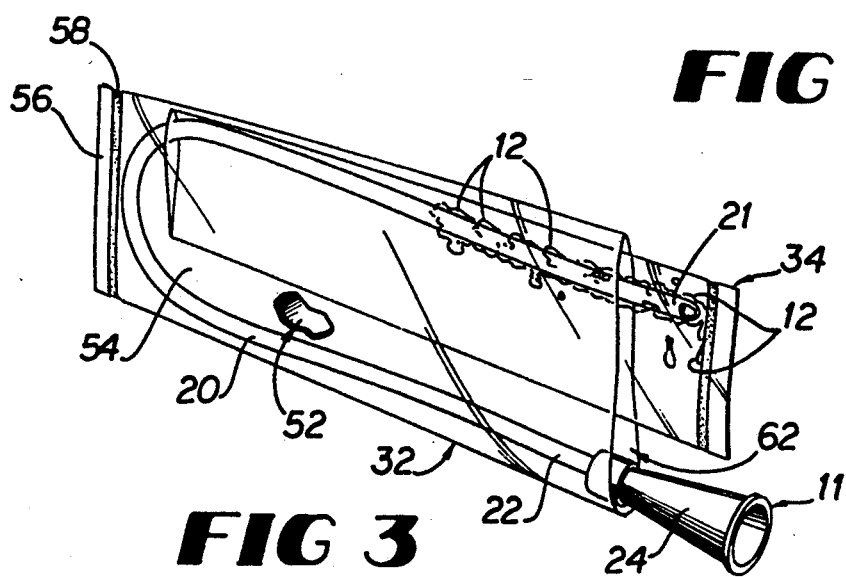
FIG. 3 is a perspective view similar to FIG. 1 with the outside enclosing receptacle removed.

Looking now at FIG. 3, the primary receptacle 32 comprises a primary tubular sheath 54 formed from a flexible heat sealable plastic tubular film with one end 56 closed such as by primary heat weld 58 to form a primary cavity 52 therein and with the opposite end open to define a primary access opening 62 to the primary cavity 52. The primary receptacle 32 enhances the handling of the catheter 11 prior to use by reducing the tendency of the lubricated projecting end to slip out of or rotate within the secondary receptacle 34 and also provides a barrier to prevent contamination of those portions of the catheter not covered by the secondary receptacle 34. The primary receptacle 32 may be sized and shaped to allow the catheter to be stowed in a U-shaped configuration resulting in a catheter unit which is more compact and which may be more easily handled than a package accommodating the catheter in a fully extended configuration. It is to be understood, however, that the particular configuration is not meant to be limiting.

Figure 2:
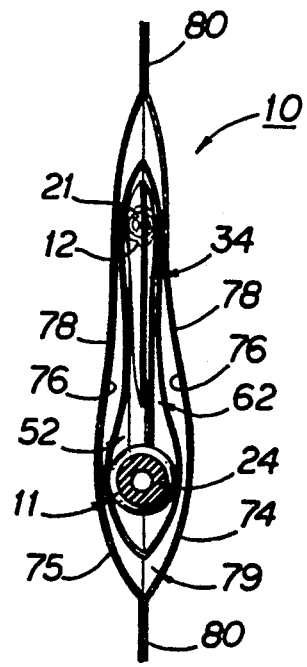
FIG. 2 is an enlarged cross-sectional view taken generally along line 2—2 in FIG. 1.

The outside enclosing receptacle 30 comprises a pair of flexible side sheets 74 and 75, with each side sheet having an interior surface 76 and an exterior surface 78 which is more clearly shown in FIG. 2. A peripheral seal 80 is formed around the overlying sheets 74 and 75 and located adjacent to the outer edges of and continuously along the perimeter of the side sheets. This seals the catheter 11 with the lubricant 12 thereon along with the receptacles 32 and 34 in the cavity 79 to complete the assembly 10 so that the contents of the outside receptacle 30 can be sterilized in conventional manner.

The catheter 11 is retrieved from the enclosing receptacle 30 by cutting open the enclosing receptable and removing the contents. Alternatively, the enclosing receptacle 30 may be fabricated to facilitate being torn open by hand by causing a portion of the seal 80 of each of the side sheets to be disposed a predetermined distance from opposing edges of each side sheet to provide tear open flaps 82. The enclosing receptacle 30 may be conveniently opened by grasping the tear open flaps 82 and pulling them apart to cause the enclosing receptacle 30 to part along the sealing surfaces 80.

Figure 5:
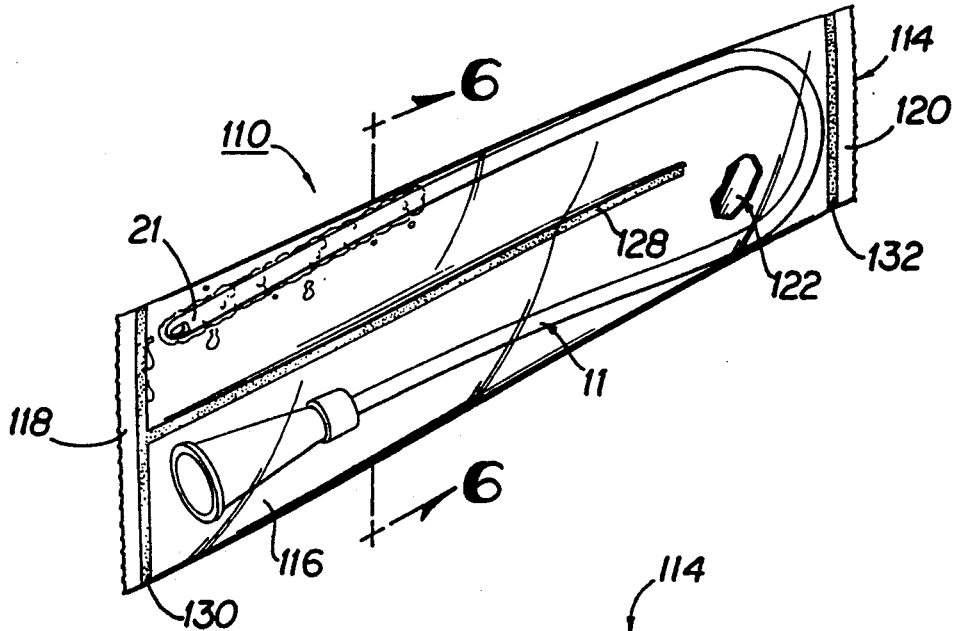
FIG. 5 is a perspective view of a second embodiment of the invention.
Figure 6:
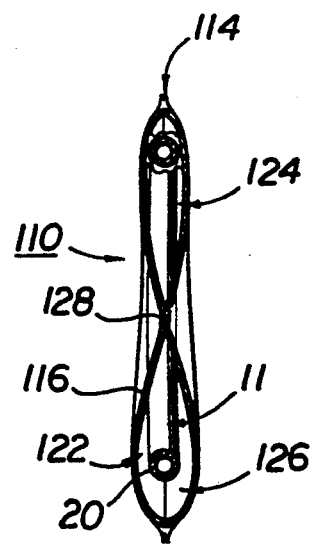
FIG. 6 is an enlarged cross-sectional view taken generally along line 6—6 in FIG. 5.

An alternative embodiment of a catheter and packaging assembly designated 110 is shown in FIGS. 5 and 6. The catheter 11 and lubricant 12 are the same as with the first embodiment of the package assembly. The package assembly 114 is changed.

The package assembly 114 comprises a single piece tubular plastic sheath 116 with opposed ends 118 and 120 defining a single catheter receiving cavity 122 therein. The catheter receiving cavity 122 is divided into a projecting end receiving first portion 124 and a discharge end receiving second portion 126 by any suitable means such as a longitudinally extending septum weld 128 joining the sides of the sheath 116 together between the projecting and discharge ends of the catheter. The prelubricated projecting end 21 of the catheter 11 is disposed within the first portion 124 and the rest of the catheter is disposed within the second portion 126 by forming the catheter 11 into a U-shaped configuration. The first end 118 of the tubular sheath 116 is sealed by a first end weld 130. The first end weld 130 is located so that a portion of the first end weld 130 intersects the septum weld 128 and is effective to isolate the lubricant 12 and the lubricated projecting end 21 from the drainage end 22 disposed in the second portion 126 of the catheter receiving cavity 122. The second end 120 of the tubular sheath 116 is also sealed by a second end weld 132 and is effective to complete the sealing of the package assembly 114 so that the entire catheter and package assembly 110 can be sterilized in conventional manner.

The catheter 11 contained in the single piece package assembly 114 may be retrieved by cutting the tubular sheath 116 adjacent to the second end weld 132, grasping the "U" shaped region of the catheter tube 20 and sliding the catheter 11 from the package assembly 114. Of course, the user may open the package assembly 114 in any convenient manner.

In those instances where the complete catheter 11 is to be coated with the lubricant 12, the prelubricated catheter is located in a single cavity in the package assembly. It is still desirable for the cavity carrying the catheter to be subdivided into different portions to keep all of the lubricant from flowing into one part of the cavity.

What is claimed as invention is:

1. A prelubricated urinary catheter and package assembly for use in draining the bladder through the urethra comprising:
    a) an elongate catheter tube defining a projecting end and a drainage end at opposite ends thereof and defining a drainage passage extending from said projecting end to said drainage end so that fluids in the bladder can drain therethrough when said projecting end of said catheter tube is inserted into the bladder through the urethra;
    b) a lubricant on the projecting end of said catheter; and
    c) a package assembly comprising:
        a flexible primary receptacle defining a primary catheter receiving cavity therein for stowing said catheter, said primary catheter receiving cavity sized and shaped to stow said catheter in a generally U-shaped configuration;
        isolation means comprising a flexible secondary receptacle defining a secondary projecting end receiving cavity therein and a secondary access opening to said secondary receiving cavity removably receiving the projecting end of said catheter with the lubricant thereon to isolate the lubricant from said primary cavity, said secondary receptacle removable from the projecting end of said catheter without removing the lubricant from said catheter, said primary receptacle defining a primary access opening to said primary cavity so that said catheter and said secondary receptacle with the projecting end of said catheter therein can be removably inserted into said primary cavity in said primary receptacle; and an enclosing receptacle defining a sterile cavity sealably receiving said primary and secondary receptacles and said catheter with the lubricant thereon therein.

2. A prelubricated urinary catheter and package assembly for use in draining the bladder through the urethra comprising:
 a) an elongate catheter tube having a projecting end and an opposite end and defining a drainage passage extending therethrough so that fluids in the bladder can drain therethrough when said projecting end of said catheter tube is inserted into the bladder through the urethra;
 b) a lubricant on said projecting end of said catheter; and
 c) a package assembly including:
  a thin flexible tubular sheath having opposed sides defining a catheter receiving cavity therein sized to hold said catheter tube in a U-shaped configuration and in which said catheter with said lubricant thereon is housed in the U-shaped configuration, and
  a septum weld sealing said sides of said tubular sheath together between the ends of the catheter so as to isolate the lubricated projecting end of the catheter from the rest of the catheter.

3. The assembly of claim 2 wherein said package assembly wherein said catheter receiving cavity has opposed ends and further includes an end weld connected to said septum weld and sealing said sides of said tubular sheath together to seal one of the ends of said catheter receiving cavity.

4. A method of packaging catheters comprising the steps of:
 a) applying a lubricant to the projecting end of the catheter and not to the drainage end of the catheter; and,
 b) enclosing the catheter in a package assembly so that the lubricant and the projecting end of the catheter is isolated from the rest of the catheter to limit the area of the catheter coated with lubricant while in the package assembly, and further comprising the substeps of:
  b1) forming the catheter in a U-shaped configuration,
  b2) inserting the catheter in the U-shaped configuration into a tubular plastic sheath, and
  b3) heat sealing the sides of the plastic sheath together between the ends of the catheter so as to isolate the lubricated projecting end of the catheter from the rest of the catheter.

5. The method of claim 4 wherein step b) comprises the further substeps of:
 b4) heat sealing the opposite ends of the plastic sheath to seal the catheter in the plastic sheath while locating one of the end heat seals so that it intersects the heat seal formed in substep b3) to help isolate the lubricated projecting end of the catheter from the rest of the catheter.

* * * * *